United States Patent [19]
Lin

[11] Patent Number: 6,094,275
[45] Date of Patent: Jul. 25, 2000

[54] APPARATUS AND METHOD FOR MEASURING OPTICAL PROPERTIES OF A COATING LAYER

[75] Inventor: Shih-Chi Lin, Taipei, Taiwan

[73] Assignee: Taiwan Semiconductor Manufacturing Company, Ltd., Hsin-Chu, Taiwan

[21] Appl. No.: 09/365,862

[22] Filed: Aug. 3, 1999

[51] Int. Cl.[7] .......................... G01B 11/00; G01N 21/00; G01N 21/55
[52] U.S. Cl. .......................... 356/445; 356/400; 356/432
[58] Field of Search .................................. 356/445, 448, 356/432, 400, 51, 237

[56] References Cited

U.S. PATENT DOCUMENTS 4,795,260   1/1989   Schuur et al. .......................... 356/400

*Primary Examiner*—Frank G. Font
*Assistant Examiner*—Armando Rodriguez
*Attorney, Agent, or Firm*—Tung & Associates

[57] ABSTRACT

A test apparatus for measuring optical properties of a coating layer on a semiconductor substrate and a method for using such apparatus are disclosed. In the apparatus, a fixed stage and a traversing stage are utilized such that a semiconductor substrate can be mounted in the traversing stage and moved about on the fixed stage without having the substrate surface touching the fixed stage. Damages such as scratches on the substrate surface can therefore be avoided. On top of the fixed stage, a plurality of indexing marks are further provided such that the same locations on each wafer measured are fixed for taking an average value across the entire surface of the wafer. A reliable and repeatable test method is thus provided to improve the fabrication process for semiconductor substrates that have coating layers deposited on top.

20 Claims, 3 Drawing Sheets

ID=6,094,275

APPARATUS AND METHOD FOR MEASURING OPTICAL PROPERTIES OF A COATING LAYER

FIELD OF THE INVENTION

The present invention generally relates to an apparatus and a method for measuring optical properties of a coating layer on a semiconductor substrate and more particularly, relates to an apparatus and a method for measuring the UV transmittance of a passivation material layer on a silicon wafer by utilizing a fixed stage and a traversing stage such that measurements made can be indexed and any possible scratch of the wafer surface can be avoided.

BACKGROUND OF THE INVENTION

In the fabrication process of an IC device, various material layers are deposited on a semiconductor substrate for different purposes such as for insulation, for electrical conduction, for passivation, etc. After the deposition of a material layer is conducted, the physical properties of the layer sometimes must be determined in order to ensure the reliability of the device fabricated. For instance, in the fabrication of an EPROM (electrically programmable read only memory) devices, a passivation layer of silicon oxynitride is frequently deposited on top of a finished device for passivation purpose. Furthermore, as a final processing step, an UV light is used to erase memory in the EPROM chip. The UV transmittance property of the final passivation layer of silicon oxynitride is therefore an important property that must be determined before a large number of wafers can be processed.

Conventionally, the UV transmittance of a material layer coated on a semiconductor wafer is conducted in a test apparatus 10 shown in FIG. 1. The test apparatus 10 is commercially supplied by the Hewlett Packard Company of Palo Alto, Calif. In the test apparatus 10, an upper platform 12 is mounted spaced-apart from a lower platform 14 by a backing plate 16 and two support columns 18. The upper platform 12 and the lower platform 14 are mounted in a parallel relationship. Mounted between the upper platform 12 and the lower platform 14 is a light reflectance device 20 that consists of two reflecting mirrors 24, 26 each with a planar surface. An incident UV beam 28 is emitted from an UV source (not shown) and is reflected upwardly by the first mirror 24 toward a window 30 in the upper platform 12. A semiconductor substrate (not shown) is positioned on the top surface 22 of the upper platform 12 with a surface to be measured facing the reflected UV beam 32. The UV beam 32 is reflected again by the surface of the semiconductor substrate into a reflected beam 34 toward the second mirror 26. The reflected UV beam 34 is finally reflected by the second mirror 26 into UV beam 38 which is received by an UV receiver/analyzer for determining the UV transmittance (or absorption) of a coating layer on the surface of the semiconductor substrate.

The test apparatus 10 shown in FIG. 1 presents several processing difficulties. First, the semiconductor substrate is positioned face down on the surface 22 of the upper platform 12 for making measurements. In order to obtain an accurate measurement, different locations on the surface of the semiconductor substrate must be measured. In the conventional apparatus 10, different measurement locations cannot be determined since there is no provision for determining such positions. Secondly, when the substrate is moved around on the surface 22 of the upper platform 12, surface scratches are inevitable which seriously affects the quality of the IC devices in the substrate. The conventional test apparatus 10 is therefore inadequate in making accurate measurements and in preventing damages to semiconductor substrates being measured.

It is therefore an object of the present invention to provide an apparatus for measuring optical properties of a coating layer on a substrate that does not have the drawbacks or shortcomings of a conventional apparatus.

It is another object of the present invention to provide an apparatus for measuring optical properties of a coating layer on a semiconductor substrate that can be used to obtain accurate and reliable data.

It is a further object of the present invention to provide an apparatus for measuring optical properties of a coating layer on a semiconductor substrate that does not damage the surface of the substrate during such measurement.

It is another further object of the present invention to provide an apparatus for measuring optical properties of a coating layer on a semiconductor wafer that utilizes a fixed stage and a traversing stage for moving a substrate on the fixed stage.

It is still another object of the present invention to provide an apparatus for measuring optical properties of a coating layer on a semiconductor substrate capable of mounting a substrate in a traversing stage such that the substrate surface to be measured does not have direct contact with the measurement apparatus.

It is yet another object of the present invention to provide an apparatus for measuring optical properties of a coating layer on a semiconductor wafer that utilizes a fixed stage with pre-marked index locations on the stage such that measurements can be indexed and repeated for high accuracy.

It is still another further object of the present invention to provide a method for measuring optical properties of a coating layer on a semiconductor wafer by mounting the wafer in a traversing stage which slidingly engaging a fixed stage and projecting an UV beam through a window in the fixed stage.

It is yet another further object of the present invention to provide an apparatus for measuring UV transmittance of a passivation layer on a silicon wafer by mounting the wafer in a traversing stage and then moving the traversing stage on a fixed stage provided with indexing marks such that measurements can be made at predetermined locations on the wafer.

SUMMARY OF THE INVENTION

In accordance with the present invention, an apparatus and a method for measuring optical properties of a coating layer on a semiconductor substrate are provided.

In a preferred embodiment, an apparatus for measuring optical properties of a coating layer on a semiconductor substrate is provided which includes a fixed stage that is suspended horizontally over and spaced-apart from a base member, the fixed stage has a window therethrough for transmitting an optical emission, a traversing stage for holding a substrate therein and for substantially exposing a first surface of the substrate to the window in the fixed stage, and a light reflectance device mounted on the base member for reflecting an incident optical emission from an optical source toward the window and a reflected optical emission from the first surface of the substrate to an optical receiver such that optical properties of a coating layer on the substrate can be determined.

In the apparatus for measuring optical properties of a coating layer on a semiconductor substrate, the fixed stage may have a length that is at least 1.5 times of a maximum dimension of the semiconductor substrate, or the fixed stage may have a length that is at least 1.5 times of a diameter of a silicon wafer. The apparatus may further include index marks on the fixed stage such that positions for optical measurements are predetermined. The window in the fixed stage may have a diameter that is sufficient for transmission of an optical emission.

In the apparatus for measuring optical properties of a coating layer, the traversing stage may be constructed of a narrow frame for holding a substrate therein with only a minimal edge area of the substrate being covered by the narrow frame, or only an edge area of less than 2 cm being covered by the narrow frame. The traversing stage may have a smooth bottom surface adapted for sliding engagement with the top surface of the fixed stage. The traversing stage may be shaped for holding a circular wafer that has a flat side. The optical properties measured may include UV transmission through a passivation layer coated on the semiconductor wafer. The light reflectance device utilized may include at least two mirrors each has a planar reflectance surface that is adjustable.

The present invention is further directed to a method for determining optical properties of a coating layer on a substrate which can be carried out by the operating steps of first providing a fixed stage suspended horizontally over and spaced-apart from a base member, the fixed stage may have a window therethrough for transmitting an optical emission, a traversing stage for holding a substrate therein and for substantially exposing a first surface of the substrate to the window in the fixed stage, and a light reflectance device mounted on the base member, then positioning the substrate in the traversing stage and positioning the traversing stage on the fixed stage with the first surface to be measured exposed in the window of the fixed stage, reflecting an incident optical emission from an optical source toward the first surface of the substrate exposed in the window by the light reflectance device, and reflecting a reflected optical emission from the first surface of the substrate exposed in the window to an optical receiver for determining optical properties of the coating layer on the first surface of the substrate.

The method for determining optical properties of a coating layer on a semiconductor substrate may further include the step of repositioning the traversing stage on the fixed stage such that optical properties at a different location on the first surface may be determined. The method may further include the step of directing an UV emission toward the first surface of the substrate exposed in the window and collecting a reflected UV emission from the first surface by an optical receiver. The method may further include the step of determining an UV transmittance of the coating layer on the first surface of the substrate by the optical receiver. The method may further include the step of sliding the traversing stage on the fixed stage for determining optical properties at different locations. The method may further include the step of adjusting the light reflectance device by adjusting an angle of reflectance by moving the two planar reflectance mirrors.

In another preferred embodiment, an apparatus for measuring UV transmittance of a passivation layer on a wafer surface is provided which includes a fixed stage suspended horizontally over and spaced-apart from a base member, the fixed stage has a window therethrough for transmitting an optical emission, a traversing stage for holding a wafer therein and for substantially exposing a first surface of the wafer through the window in the fixed stage, an UV source for emitting an UV emission toward a light reflectance device, a light reflectance device mounted on the base member for reflecting an incident UV emission from the UV source toward the first surface exposed in the window, and for reflecting a reflected UV emission from the first surface, and an UV receiver for receiving the reflected UV emission and for determining an UV transmittance of the passivation layer coated on the first surface.

In the apparatus for measuring UV transmittance of a passivation layer on a wafer surface, the traversing stage may have a smooth bottom surface for slidingly engaging a top surface of the fixed stage without scratching the first surface of the wafer. The fixed stage may have a length that is at least 1.5 times a diameter of the semiconductor wafer.

BRIEF DESCRIPTION OF THE DRAWINGS

These and other objects, features and advantages of the present invention will become apparent upon consideration of the specification and the appended drawings, in which.

DETAILED DESCRIPTION OF THE PREFERRED EMBODIMENT

The present invention discloses an apparatus and a method for measuring optical properties of a coating layer on a semiconductor substrate such as a semiconductor wafer. The apparatus is equipped with a fixed stage suspended over a light reflectance device, and a traversing stage for sliding on top of the fixed stage for holding a semiconductor wafer therein such that the surface to be measured is substantially exposed to a window provided in the fixed stage. The fixed stage is further provided with a plurality of index marks on a top surface of the stage such that accurate measurements at predetermined locations on the substrate can be made. By utilizing the present invention novel apparatus, the surface to be measured on the semiconductor substrate does not contact the fixed stage directly so that damage to the substrate surface can be avoided.

The fixed stage utilized in the present invention apparatus should have a length that is at least 1.5 times of the maximum dimension of the semiconductor substrate to be measured. For instance, when the semiconductor substrate to be measured is a silicon wafer, the length of the fixed stage should be about 1.5 times that of the diameter of the silicon wafer such that the complete surface area of the silicon wafer can be covered by the window provided in the fixed stage for measurement.

Figure 1:
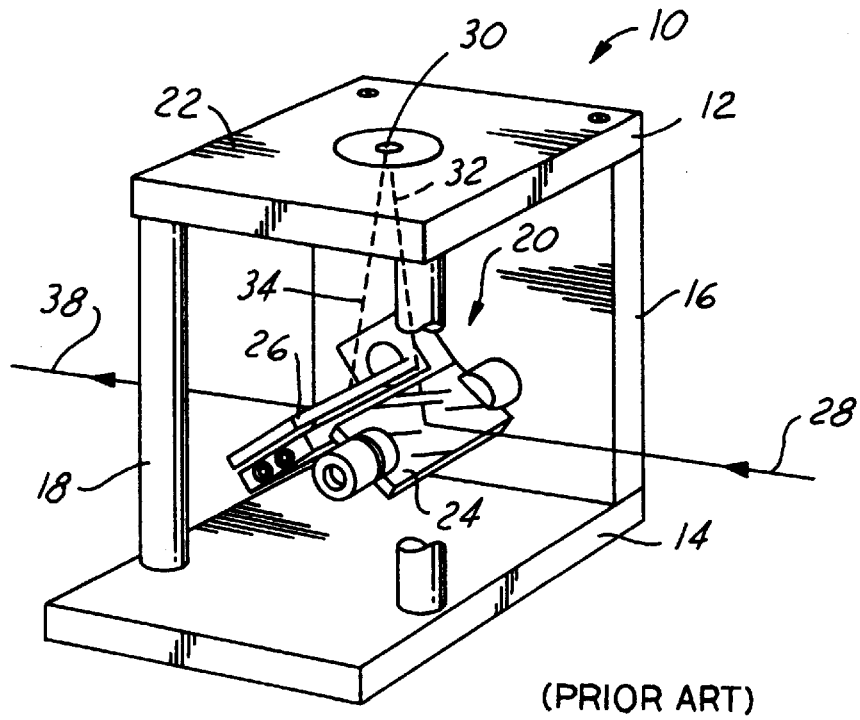
FIG. 1 is a perspective view of a conventional test apparatus for determining the optical properties of a coating layer on a substrate.
Figure 2:
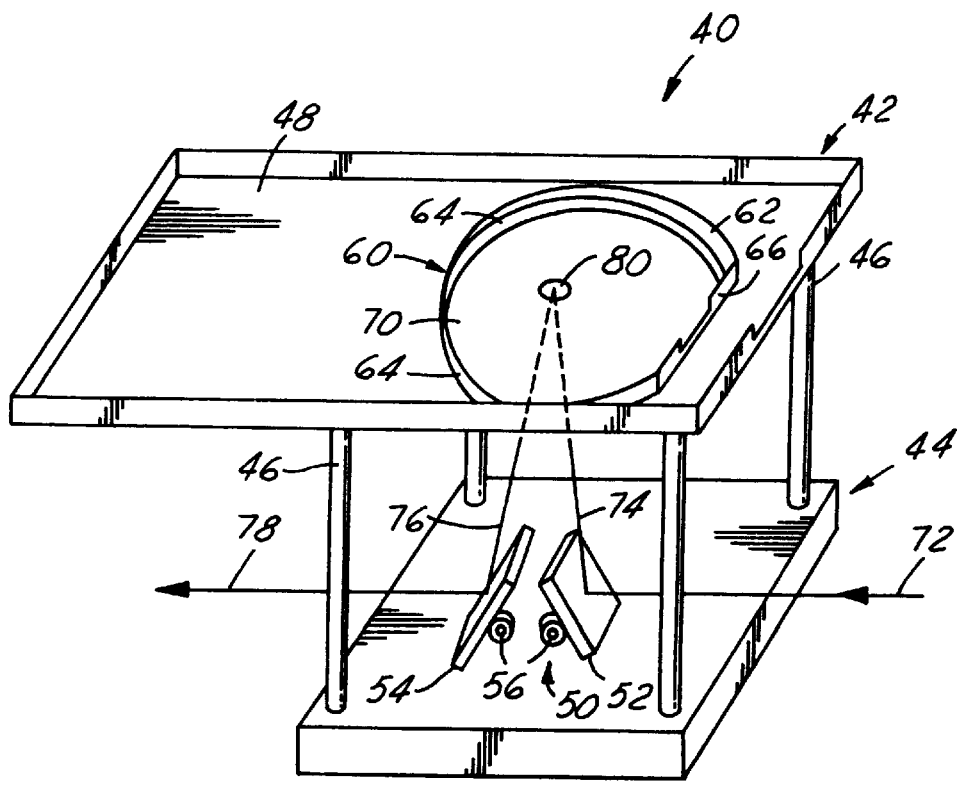
FIG. 2 is a perspective view of the present invention test apparatus equipped with a fixed stage and a traversing stage.

Referring now to FIG. 2 wherein a present invention novel test apparatus 40 is shown. The test apparatus 40 is constructed of a fixed stage 42 that is suspended over and spaced-apart from a base member 44, and supported by support columns 46. A light reflectance device 50 consists of two planar mirrors 52, 54 which are controlled by tilting mechanism 56 for changing the angles of the mirrors independently from each other. Inside the fixed stage 42, a traversing stage 60 is provided which is constructed by a narrow frame consisting of a side frame 62 and a bottom frame 64 connected in a L-shape. The traversing stage 60 shown in FIG. 2 is designed for a silicon wafer, such as a six inch diameter wafer that has a flat side for fitting the flat side 66 of the stage. The thickness of the bottom frame 64 may be in the range of about 0.5~5 mm such that when a wafer is positioned snugly in the cavity 70 formed by the side frame 62, the bottom surface of the wafer (not shown) does not touch the top surface 48 of the fixed stage 42. This is one of the novel features of the present invention apparatus in that the construction of the traversing stage permits a wafer to be moved about on the fixed stage without scratching or causing any other surface damages to the wafer.

In the present invention novel test apparatus 40 shown in FIG. 2, an incident UV beam 72 is emitted from a light source (not shown) in a direction parallel to the base member 44 and is deflected by the first mirror 52 upwardly into a reflected beam 74. The angle of the first mirror 52 is adjusted by the gear mechanism 56 such that the reflected beam 74 pointing upwardly into the opening 80 that is provided in the fixed stage 42. The opening 80 is provided with a diameter sufficiently large to allow the reflected UV beam 74 to penetrate therethrough and be projected on the bottom surface of a wafer positioned in the traversing stage 60. It should be noted that the wafer is not shown in FIG. 2. After the reflected UV beam 74 intersects the bottom surface of the wafer which has a coating layer deposited thereon, a reflected beam 76 is bounced back by the wafer surface into the second mirror 54, and then reflected again into UV beam 78 which is received by an optical receiver/analyzer. By comparing the intensity of the incident beam 72 and the intensity of the reflected beam 78, the UV transmittance of the coating layer on the wafer surface (or the amount of UV light that is not absorbed) can be calculated. To successfully erase memory through a passivation layer such as silicon oxynitride coated on an EPROM device, the passivation layer must be sufficiently transparent to UV emission with minimal absorption.

Figure 3A:
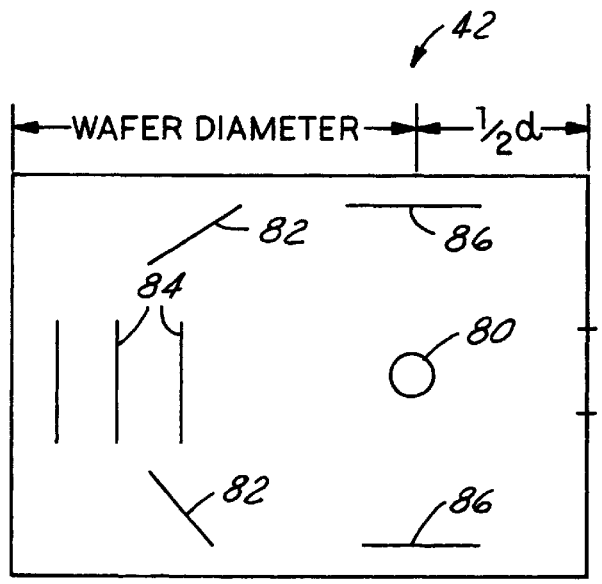
FIG. 3A is a plane view of the present invention fixed stage illustrating the indexing marks and the window.
Figure 5:
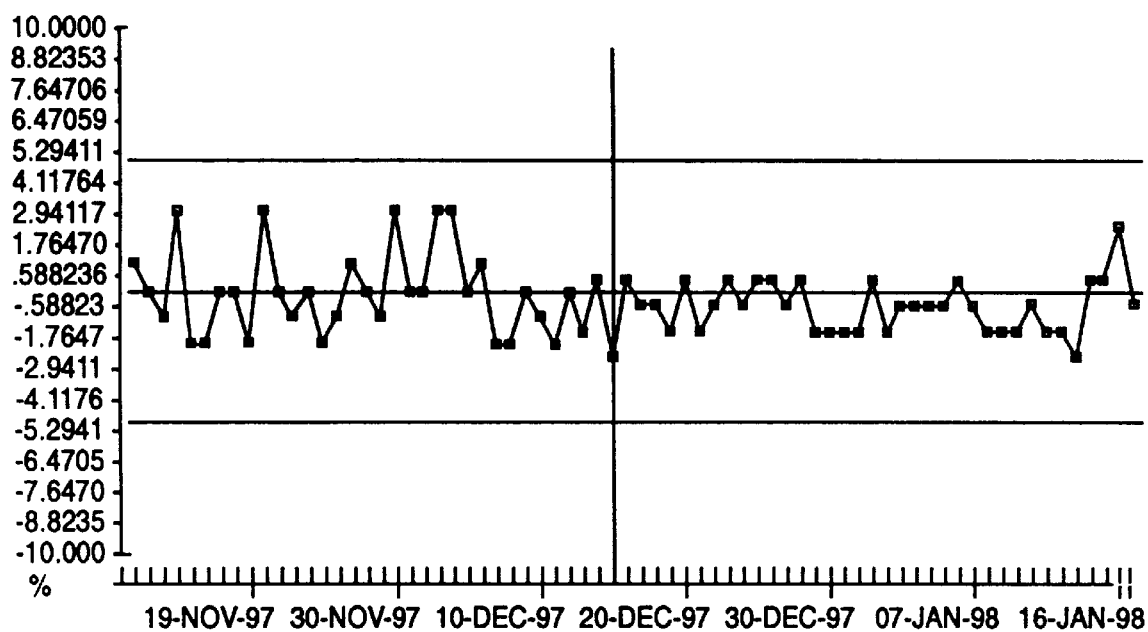
FIG. 5 is a graph of test data illustrating the effectiveness of the present invention test apparatus.

Another important aspect of the present invention novel apparatus is the capability of performing repeatable readings on a wafer surface at predetermined, indexed locations. This is shown in FIG. 3A. The index marks 86 keep the traversing stage 60 centered relative to the opening 80. The index marks 82, 84 identifies predetermined locations on the wafer surface for obtaining readings. By utilizing these index marks, any suitable number of readings can be obtained at predetermined locations on a wafer surface such that an average reading across the entire surface of the wafer can be obtained. By utilizing the present invention novel apparatus, more reliable readings can be obtained on a large number of wafers. For instance, FIG. 5 is a graph illustrating scattering of data prior to and after the implementation of the present invention novel method.

Figure 4A:
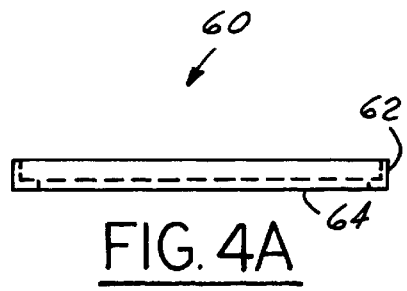
FIG. 4A is a side view of the present invention traversing stage for holding a semiconductor wafer.
Figure 4B:
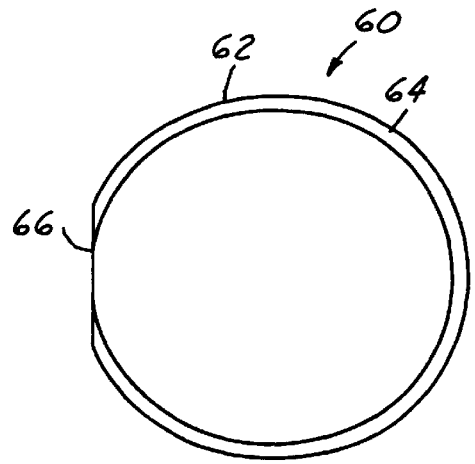
FIG. 4B is a plane view of the present invention traversing stage.
Figure 3B:
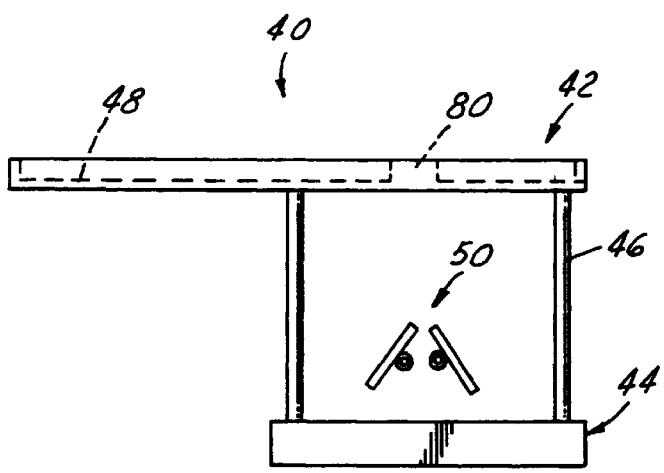
FIG. 3B is a front view of the present invention test apparatus illustrating the positioning of the light reflectance device.

A side elevation view of the present invention novel apparatus 40 is shown in FIG. 3B illustrating the location of the opening 80 in the fixed stage 42. FIG. 4A shows a side view of the traversing stage 60 and its side wall 62 and bottom wall 64. A plane view of the traversing stage 60 is shown in FIG. 4B.

The present invention novel apparatus and a method for using the apparatus have therefore been amply described in the above descriptions and in the appended drawings of FIGS. 2~5.

While the present invention has been described in an illustrative manner, it should be understood that the terminology used is intended to be in a nature of words of description rather than of limitation.

Furthermore, while the present invention has been described in terms of a preferred embodiment thereof, it is to be appreciated that those skilled in the art will readily apply these teachings to other possible variations of the invention.

The embodiment of the invention in which an exclusive property or privilege is claimed are defined as follows.

What is claimed is:

1. An apparatus for measuring optical properties of a coating layer on a substrate comprising:

a fixed stage suspended horizontally over and spaced-apart from a base member, said fixed stage having a window therethrough for transmitting an optical emission, a traversing stage for holding a substrate therein and for substantially exposing a first surface of sad substrate to said window in the fixed stage, and a light reflectance device mounted below said fixed stage for reflecting an incident optical emission from an optical source toward said window and for reflecting a reflected optical emission from said first surface of said substrate to an optical receiver such that optical properties of a coating layer on said substrate is determined.

2. An apparatus for measuring optical properties of a coating layer on a substrate according to claim 1, wherein said fixed stage has a length that is at least 1½ times of a maximum dimension of said substrate.

3. An apparatus for measuring optical properties of a coating layer on a substrate according to claim 1, wherein said fixed stage has a length that is at least 1½ times of a diameter of a semiconductor wafer.

4. An apparatus for measuring optical properties of a coating layer on a substrate according to claim 1 further comprising index marks on said fixed stage such that positions for optical measurements are fixed.

5. An apparatus for measuring optical properties of a coating layer on a substrate according to claim 1, wherein said window in said fixed stage has a diameter that is sufficient for the transmission of an optical emission.

6. An apparatus for measuring optical properties of a coating layer on a substrate according to claim 1, wherein said traversing stage is a narrow frame for holding a substrate therein with only a minimal edge area being covered by said narrow frame.

7. An apparatus for measuring optical properties of a coating layer on a substrate according to claim 1, wherein said traversing stage is a narrow frame for holding a wafer therein with only an edge area of less than 2 cm being covered by said narrow frame.

8. An apparatus for measuring optical properties of a coating layer on a substrate according to claim 1, wherein said traversing stage haw a smooth bottom surface adapted for sliding engagement with said top surface of the fixed stage.

9. An apparatus for measuring optical properties of a coating layer on a substrate according to claim 1, wherein said traversing stage is shaped to hold a circular wafer that has a flat side.

10. An apparatus for measuring optical properties of a coating layer on a substrate according to claim 1, wherein said optical properties measured comprises UV transmission through a passivation layer coated on a semiconductor wafer.

11. An apparatus for measuring optical properties of a coating layer on a substrate according to claim 1, wherein said light reflectance device comprises at least two mirrors each having a planar reflectance surface that is adjustable.

12. A method for determining optical properties of a coating layer on a substrate comprising the steps of:

providing a fixed stage suspended horizontally over and spaced-apart from a base member, said fixed stage having a window therethrough for transmitting an optical emission, a traversing stage for holding a substrate therein and for substantially exposing a fist surface of said substrate to said window in the fixed stage, and a light reflectance device mounted below said fixed stage, positioning said substrate in said traversing stage and then positioning said traversing stage on said fixed stage with said first surface to be measured exposed in said window of the fixed stage, reflecting an incident optical emission from an optical source toward said first surface of the substrate exposed in said window by said light reflectance device, and reflecting a reflected optical emission from said first surface of the substrate exposed in said window to an optical receiver for determining optical properties of said coating layer on said first surface of the substrate.

13. A method for determining optical properties of a coating layer on a substrate according to claim 12 further comprising the step of repositioning said traversing stage on said fixed stage such that optical properties at a different location on said first surface is determined.

14. A method for determining optical properties of a coating layer on a substrate according to claim 12 further comprising the step of directing an UV emission toward said first surface of the substrate exposed in said window and collecting a reflected UV emission from said first surface by an optical receiver.

15. A method for determining optical properties of a coating layer on a substrate according to claim 14 further comprising the step of determining an UV transmittance of said coating layer on said first surface of the substrate by said optical receiver.

16. A method for determining optical properties of a coating layer on a substrate according to claim 12 further comprising the step of sliding said traversing stage on said fixed stage for determining optical properties at different locations.

17. A method for determining optical properties of a coating layer on a substrate according to claim 12 further comprising the step of adjusting said light reflectance device by adjusting an angle of reflectance by moving two planar reflectance mirrors.

18. An apparatus for measuring UV transmittance of a passivation layer on a wafer surface comprising:

a fixed stage suspended horizontally over and spaced-apart from a base member, said fixed stage having a window therethrough for transmitting an optical emission, a traversing stage for holding a wafer therein and for substantially exposing a first surface of said wafer through said window in the fixed stage, an UV source for emitting an UV emission toward a light reflectance device, a light reflectance device mounted below said fixed stage for reflecting an incident UV emission from said UV source toward said first surface exposed in said window, and for reflecting a reflected UV emission from said first surface, and an UV receiver for receiving said reflected UV emission and for determining an UV transmittance of said passivation layer coated on said first surface.

19. An apparatus for measuring UV transmittance of a passivation layer on a wafer surface according to claim 18, wherein said traversing stage has a smooth bottom surface for slidingly engaging a top surface of said fixed stage without scratching said first surface of the wafer.

20. An apparatus for measuring UV transmittance of a passivation layer on a wafer surface according to claim 18, wherein said fixed stage has a length that is at least 1.5 times a diameter of said wafer.

* * * * *